United States Patent [19]

Ferruti et al.

[11] 4,093,677
[45] June 6, 1978

[54] MACROMOLECULAR MATERIALS SUITABLE FOR FORMING ANTITHROMBOGENIC PROSTHESIS AND ARTIFICIAL ORGANS AND PROCESS FOR PREPARING SAME

[76] Inventors: Paolo Ferruti, V. le Cassiodoro 24, Milan; Ezio Martuscelli, Vico Monteroduni 8; Fernando Riva, Via Trigergola 2, both of Naples; Luciano Provenzale, P.za dei Servili 2, Rome, all of Italy

[21] Appl. No.: 778,454

[22] Filed: Mar. 17, 1977

Related U.S. Application Data

[63] Continuation-in-part of Ser. No. 694,394, Jun. 6, 1976, abandoned.

[30] Foreign Application Priority Data

Jun. 10, 1975 Italy ............................. 24245 A/75

[51] Int. Cl.² ................... C08L 77/00; C08L 75/00
[52] U.S. Cl. ............................ 260/858; 260/857 UN; 260/857 TW; 260/857 PE; 260/857 G
[58] Field of Search ............... 260/857 UN, 857 TW, 260/857 PE, 857 G, 858

[56] References Cited

U.S. PATENT DOCUMENTS

| 3,668,278 | 6/1972 | Bonvicini | 260/857 UN |
| 3,766,138 | 10/1973 | Crivello | 260/857 UN |
| 3,773,739 | 11/1973 | Bonvicini | 260/78 A |
| 3,865,723 | 2/1975 | Antonietta | 210/54 C |

Primary Examiner—Paul Lieberman
Attorney, Agent, or Firm—Browdy and Neimark

[57] ABSTRACT

Novel block copolymers suitable to manufacture permanently antithrombogenic prosthetic devices are obtained by first preparing a polyamide-amine prepolymer

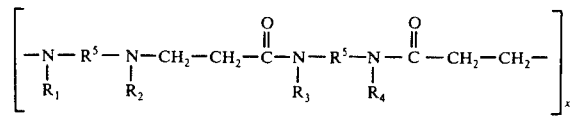

or

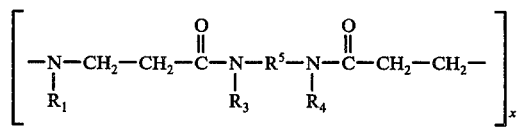

wherein $R_1$ and $R_2$ are alkyl or hydroxy-alkyl radicals with 1–6 carbon atoms, $R_3$ and $R_4$ are alkyl radicals with 1–6 carbon atoms, $R_5$ is an alkenyl radical with 1–12 carbon atoms, or together with $R_1$, $R_2$ and $R_3$, $R_4$ respectively and the nitrogen atoms to which it is linked, it forms an unsubstituted or substituted piperazine ring and then polymerizing at least one monomer suitable to form thermoplastic addition or condensation polymers in the presence of the polyamide-amine prepolymer.

16 Claims, No Drawings

MACROMOLECULAR MATERIALS SUITABLE FOR FORMING ANTITHROMBOGENIC PROSTHESIS AND ARTIFICIAL ORGANS AND PROCESS FOR PREPARING SAME

REFERENCE TO RELATED APPLICATION

The present application is a continuation-in-part of U.S. application Ser. No. 694,394 filed June 6, 1976, now abandoned the entire contents of which are hereby incorporated by reference.

FIELD OF THE INVENTION

The present invention relates to novel macromolecular materials highly useful in the biomedical field for the manufacture of prostheses and artificial organs, and also relates to a process for preparing same.

More particularly, the present invention relates to novel block copolymers which not only possess excellent characteristics of thermoformability upon extrusion, molding and similar processes, but are also able to permanently fix heparin. Consequently, these novel copolymers are suitable for producing upon extrusion, molding and similar processes, permanently antithrombogenic prostheses and artificial organs.

DESCRIPTION OF THE PRIOR ART

It is known that at present the major limiting factor in the use of polymeric materials for prosthetic devices and artificial organs is the thrombogenic action exerted in larger or smaller extent by these materials when they are in contact with blood.

It is also known that heparin is a polyanion endowed with excellent blood anticoagulant properties.

During the last years, it has been on several occasions suggested to make antithrombogenic the surfaces of polymeric materials by absorption of heparin onto their surfaces. In practice, however, it has been constantly found that the various polymers either are not able to establish chemical bonds with heparin or they form extremely weak bonds. It has been also suggested to form stable, indirect bonds between the polymer surface and heparin by preliminary absorption onto the polymer material of quaternary ammonium salts, if the case may be after a graphitization step, and subsequent bonding of heparin to the polymer material thus treated. In practice this method has proved to be unsatisfactory both because of the propensity of the ammonium salts for becoming disabsorbed and because of the hemolytic activity generally shown by the compounds containing quaternary ammonium groups, which exert a harmful action on thrombocytes. Besides, this method has proved not to be applicable to flexible materials. In the U.S. Pat. No. 3,865,723 to Marchisio et al. there is disclosed that a group of macromolecular materials having the character of polyamide-amines comprising tertiary amine groups are able to highly selectively adsorb heparin from blood and other biological fluids by forming stable complexes, without exerting any action either on the plasma proteins or the blood corpuscles.

These polymers, however, have proved to be unsuitable to form materials for prosthesis, insofar as they are endowed with unsatisfactory mechanical properties and high water-solubility, unless they are cross-linked.

SUMMARY OF THE INVENTION

Novel polymers having block structure have now been found, which not only possess excellent characteristics of thermoformability and result in articles with excellent mechanical properties, but also are able to fix directly and permanently heparin onto their surfaces, thus acquiring thrombo-resistant properties.

The novel polymers are characterized by the presence in their molecular structure of both polyamidic-aminic blocks and blocks of conventional thermoplastic polyaddition and polycondensation polymers, such as vinyl polymers, vinilydene polymers, polyamides, polyesters, polyureas, polyurethanes and the like.

It has been surprisingly found that the novel polymers have physical and mechanical characteristics essentially equivalent to those of the polyaddition and polycondensation polymers forming the blocks having conventional structure, whilst they have such chemical properties as to permit the direct formation of stable complexes with heparin, which property is caused by the polyamidic-aminic blocks. The novel polymers are water-insoluble and behave like themoplastic materials which can be worked by conventional molding, extrusion and the like techniques. The articles thus obtained adsorb on their surfaces heparin from its water or hydroalchoolic solutions at pH ranging between 0 to 9, steadily fixing it, thus permanently acquiring antithrombogenic properties.

Since the novel antithrombogenic articles do not contain any other compound and particularly do not comprise quaternary ammonium groups, they do not present any one of the foregoing disadvantages which have so far hindered the macromolecular materials having heparinized surfaces from being utilized in the biomedical field.

The process for preparing the novel polymers comprises the following steps:
(a) preparing polyamide-amines having the desired polymerization degree;
(b) polymerizing the monomer or the mixture of monomers which are suitable to produce the conventional polyaddition or polycondensation polymers, in the presence of the preformed polyamide-amines.

DESCRIPTION OF THE PREFERRED EMBODIMENTS

The poly-amide-amines useful in the present invention are obtainable essentially by polyaddition of disecondary bis-amines or primary monoamines to bis-acrylamides according to the reactions

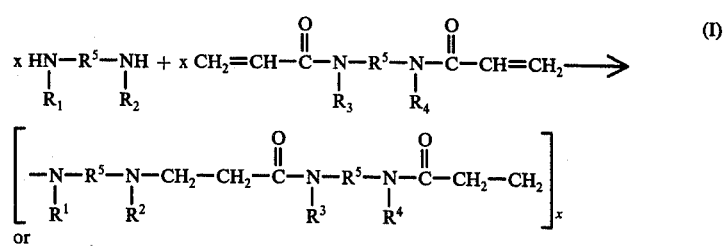

-continued

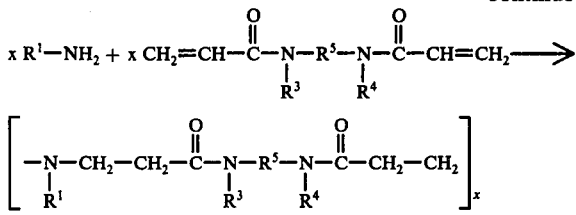

$$\left[ -N-CH_2-CH_2-\overset{O}{\underset{R^3}{\overset{\|}{C}}}-N-R^5-N-\overset{O}{\underset{R^4}{\overset{\|}{C}}}-CH_2-CH_2 \right]_x$$

wherein: $R^1$ and $R^2$ are alkyl or hydroxyalkyl radicals having 1-6 carbon atoms, $R^3$ and $R^4$ are alkyl radicals having 1-6 carbon atoms, $R^5$ is an alkenyl radical having 1-12 carbon atoms or together with $R^1$, $R^2$ and $R^3$, $R^4$ respectively, and the nitrogen atoms to which it is bonded forming a substituted or an unsubstituted piperazine ring.

The number average polymerization degree of these products can be predetermined by the ratio between the two types of chemical function (vinyl and amine function) in the starting monomer mixture, from the formula $$\overline{X}_n = (1 + \mu)/(1 - \mu)$$

and hypothesizing, what in this case appears reasonable, that the polyaddition reaction proceeds to completion.

By operating with an excess amount of bis-acrylamides or amines it is possible to obtain polyamide-amines having vinyl end groups, respectively amine end groups.

It has been found that the polyamide-amines having vinyl end groups are useful for preparing the novel block polymers of this invention, wherein the blocks of conventional polymers have polyvinyl or polyvinylidene character.

In fact, this type of polyamide-amines if mixed with vinyl or vinylidene monomers, such as styrene, ring-substituted styrenes, alkylacrylates, alkylmethacrylates, acrylamide and substituted acrylamides, vinyl acetate, acrylonitrile and the like, under the polymerization conditions suitable for these latter monomers, take part in the reaction with their end groups, thus giving rise to the novel block polymers.

It has also been found that polyamide-amines having secondary amine end groups, if mixed with mixtures of monomers suitable to form polyamides, polyesters, polyureas, polyurethanes, and the like, and brought to the conditions suitable for the formation of these latter polymers, take part in the polyaddition or polycondensation reaction with their amine end groups, thus forming the novel block polymers of this invention. It was previously stated that the polyamide-amines useful in the present invention are obtainable "essentially" by polyaddition of disecondary bis-amines or primary monoamines to bis-acrylamides, insofar as in practice, apart from these essential monomers, they can comprise other monomers containing other chemical functions, provided that in such monomers also the groups necessary for the polyaddition (amine and acrylyl groups) are present. Examples of such monomers are: piperazine mono- and di-carboxyl acids, aliphatic amino-acids having 1-6 carbon atoms, allyl-amine, primary diamines containing 2-12 atoms.

However, the addition to the polymerization mixture of the foregoing or similar monomers does not lead to particular advantages as far as the power of fixing heparin shown by the ultimate polymers is concerned, and consequently no particular advantages can be achieved by thus complicating the structure of the polyamide-amines and therefore of the novel polymers of this invention.

In order to prepare the polyamide-amines according to the present invention the selected monomers are dissolved in water or in an hydroxylated organic solvent, preferably an alcohol, and the mixture is allowed to polymerize at temperatures of from 10° to 50° C, with reaction time ranging between a few hours (3-4 hours) to some days (3-5 days) depending on the monomers which are used. The preparation methods, however, will be clearly apparent from the herebelow illustrated examples.

As previously indicated, the processes for preparing the novel block copolymers are substantially those used for polymerizing the monomers making up the conventional polymer blocks and are therefore selected everytime depending on the monomer or monomer mixture to be copolymerized with the preformed polyamide-amines.

Also these processes will be clearly apparent from the herebelow illustrated examples.

The heparin adsorption on the surfaces of articles such as tubings, films, yarns, fibers, etc. consisting of the foregoing materials, takes place by simply contacting the articles for time periods varying from 2 to 100 minutes with alchoolic, hydroalchoolic or water solutions of heparin, having concentration of 0.1-20% and pH value of from 0 to 9. Sometimes, a previous treatment of the articles with acids such as hydrochloric acid, acetic acid etc., in hydroalchoolic or water solution, at concentration varying between 0.1 and 20%, can be carried out.

The adsorbed heparin can be cross-linked with glutaric aldehyde or other aldehydes, to render even more difficult the heparin disadsorption from the article surfaces under the conditions of use prevailing in a biological environment.

The various aspects of the present invention will be more apparent from the following illustrative examples which should not be construed as to limit the scope of the invention.

EXAMPLE 1

(A) 19.4238 grams of 1,4-bis acrylylpiperazine were dissolved in 48.75 millimeters of an 1-molar aqueous solution of N,N'-dimethylendiamine which had been titrated by acidimetry. The molar ratio ($\mu$) of the two reagents was 0.975. From a theoretical standpoint, that should lead to a product having number average polymerization degree $\overline{X}_n$ equal to 79. The mixture was allowed to stand at room temperature for four days. The mixture was then poured into an excess amount of acetone and allowed to stand for a few hours. The product crystallized and was separated by filtration. A polyamide-amine was obtained (yield = 95%) having the formula

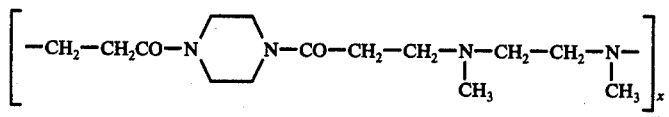

with end groups of the following kind

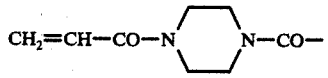

The number average polymerization degree, determined by osmometry, was found to be in good agreement with the theoretically anticipated value. By following precisely the same procedures, there were prepared polyamide-amines with vinyl end groups and number average polymerization degrees ranging from 10 to 300 (by varying the molar ratio $\mu$ of bis-acrylamides to amines in the monomer mixture in the range of from 0.818 to 0.993), starting from the following bis-acrylamides:

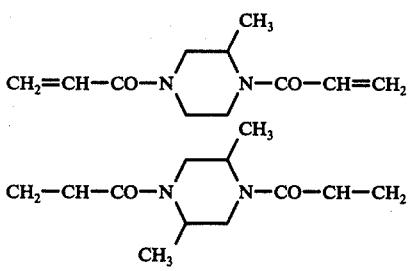

CH$_2$=CH—CO—NH—CH$_2$—NH—CO—CH=CH$_2$
CH$_2$=CH—CO—NH(CH$_2$)$_2$NH—CO—CH=CH$_2$
CH$_2$=CH—CO—NH(CH$_2$)$_3$NH—CO—CH=CH$_2$
CH$_2$=CH—CO—NH(CH$_2$)$_4$NH—CO—CH=CH$_2$
CH$_2$=CH—CO—NH(CH$_2$)$_{12}$NH—CO—CH=CH$_2$ $$\text{CH}_2=\text{CH}-\text{CO}-\underset{\underset{\text{CH}_3}{|}}{\text{N}}-\text{CH}_2-\text{CH}_2-\underset{\underset{\text{CH}_3}{|}}{\text{N}}-\text{CO}-\text{CH}=\text{CH}_2$$

$$\text{CH}_2=\text{CH}-\text{CO}-\underset{\underset{\text{C}_2\text{H}_5}{|}}{\text{N}}-\text{CH}_2-\text{CH}_2-\underset{\underset{\text{C}_2\text{H}_5}{|}}{\text{N}}-\text{COCH}=\text{CH}_2$$

$$\text{CH}_2=\text{CH}-\text{CO}-\underset{\underset{\underset{(\text{CH}_3)_2}{|}}{\text{CH}}}{\text{N}}-\text{CH}_2-\text{CH}_2-\underset{\underset{\underset{(\text{CH}_3)_2}{|}}{\text{CH}}}{\text{N}}-\text{CO}-\text{CH}=\text{CH}_2$$

and from the following amines:

CH$_3$NH$_2$, C$_2$H$_5$NH$_2$, C$_3$H$_7$NH$_2$, (CH$_3$)$_2$CH—NH$_2$,

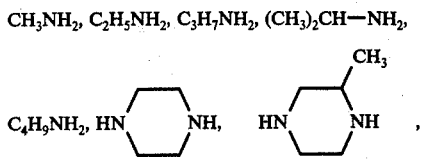

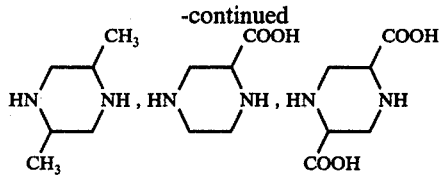

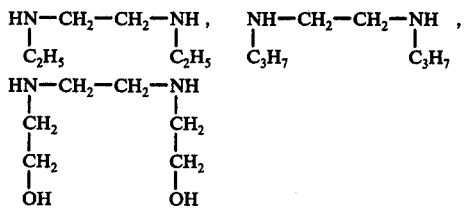

Instead of pure bis acrylamides and pure amines, mixtures of bis-acrylamides and mixtures of amines were also employed, if that be the case also with other monomers of the indicated type (piperazine mono- and di-carboxylic acids and aliphatic amino-acids with 1-6 carbon atoms, allyl-amines, primary di-amines having from 2 to 12 carbon atoms); in any case, however, keeping the ratio of the bis-acrylamide monomers to amine monomers within the above indicated range.

(B) 20 grams of poly-amide -amine of the formula

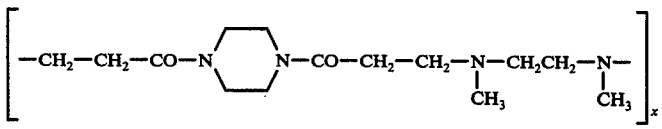

having $X_n$ = 79 and vinyl type end groups, prepared according to the procedures shown in paragraph (A), were dissolved in 60 millimeters of a 8:2 dioxane:ethanol mixture, 14 grams of styrene per gram of polyamide-amine were added to 1.5 gram of azodiisobutyronitrile. The mixture was then heated for 24 hours at 60° C in a thermostatic bath. Subsequently the mixture was poured in a 1:1 ether/heptane mixture, and the precipitated product was recovered. 145 grams of a block copolymer having prevailingly the following structure

were obtained, wherein the central block has the above-indicated poly-amidic-aminic structure, whilst the side blocks have polystyrene structure:

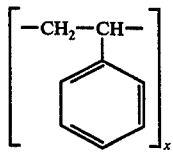

The product was analyzed and showed a nitrogen content of 1.70%, corresponding to 8.57% by weight of poly-amidic-aminic blocks. It was found that the behaviour towards solvents of the novel polymer (subsequently referred to as PAA-1) practically coincides with that of polystyrene, whilst it is considerably different from that of the poly-amide-amine. Comparison tests were carried out in which the polymers were ri-precipitated from their solutions in a common solvent with alchools and cyclohexane which are specific precipitating agents for polystyrene and poly-amide-amine, respectively. A solution containing 2.5% of PAA-1 in methylene chloride was poured in 5 volumes of isobutyl alchool and n-octyl alchool, respectively. In both cases, an intense opalescence was obtained, but with no apparent flocculation even after 7 days the mixture was allowed to stand. Under the same conditions, a solution containing 2.5% in methylene chloride of a mixture of polystyrene ($\overline{M}_v$ = 34,000) and the same previously employed poly-amide-amine at a ratio of 10:1 by weight gave flocculent precipitates which settled completely after 8 hours the mixture was allowed to stand. On the other hand, the same PAA-1 solution, poured in 5 volumes of cyclohexane, gave a perfectly clear mixture, whilst the same solution of polystyrene and poly-amide-amine, when poured in 5 volumes of cyclohexane gave a precipitate which could be separated by decantation. From all the aboveindicated tests of solubility and ri-precipitation, one could come to the conclusion that no free poly-amide-amine was present in the PAA-1 product.

It was not possible, however, to categorically exclude the presence of traces of free polystyrene. From the stand point of its mechanical properties, the PAA-1 product turned out to be a thermoplastic material, which was mouldable with some increased difficulty with respect to polystyrene, but substantially under the same conditions.

(C) By an especially made mould of chromium plated brass, some cylindrical, hollow test pieces were prepared using the PAA-1 polymer, manufactured as shown in the preceding paragraph. The test pieces were 25 millimeters long with a 15 millimeters inner diameter and a 20 millimeters outer diameter. The test pieces were heparinized by pre-treatment with a 5% alchoolic solution of acetic acid (in order to ionize the amine groups), followed by treatment with a 1:1 water/ethanol solution containing 10% of heparin, followed by treatment with an aqueous solution containing 2.5% of glutaric aldehyde (in order to fix heparin by partial crosslinking), and finally by repeated and accurate washings with distilled water. The test pieces were then implanted in the inferior vena cava of a test animal (dog) in accordance with the procedures of the thromboresistance test largerly accepted in the biological field (in this connection, reference is made to "Antithrombogenic surfaces, classification and in vivo evaluation", Vincent L. Gott and Akira Furuse, Federation Proceedings Vol. 30, No. 5, September–October 1971). The rings of the substance under examination were removed after 2 weeks and showed very slight, unsteady traces of thrombosis only at the joints, whilst the ring hole had remained completely pervious; the control test pieces of polystyrene were massively thrombosed with clogging of the ring hole. Therefore, it could be concluded that the surface of the test pieces of PAA-1, was, after heparinization, permanently thrombo-resistant. Following the same procedures, the other copolymers listed in the table I were prepared, starting from a poly-amide-amine obtained as previously described, but using a 0.983 molar ratio between bis-amine and bis-acrylamide. The subsequent step was performed as in the case of PAA-1, but adding to the poly-amido-amine solution different amounts of styrene and azodiiso-butyronitrile.

Table I

| Block copolymers | Mn of the poly-amido-amine blocks | N % | Percent by weight of poly-amido-amine blocks |
|---|---|---|---|
| PAA-1 | 10.000 | 1.70 | 8.57 |
| PAA-2 | 16.000 | 1.78 | 8.97 |
| PAA-3 | " | 3.20 | 16.10 |
| PAA-4 | " | 4.22 | 21.27 |
| PAA-5 | " | 5.07 | 25.55 |
| PAA-6 | " | 6.65 | 33.52 |
| PAA-7 | " | 9.84 | 49.60 |
| PAA-8 | " | 12.78 | 64.35 |
| PAA-9 | " | 12.85 | 64.85 |
| PAA-10 | " | 15.90 | 80.00 |
| PAA-11 | " | 16.46 | 82.80 |

In the following table II, the solubility data of the PAA-1 block copolymer, of the poly-amido-amine used in its preparation and of polystyrene are indicated.

Table II

| Solvent | Behaviour * | | |
|---|---|---|---|
| | PAA-1 ** | Poly-amido-amine ** | Polystyrene ** |
| n-heptane | I | I | I |
| benzene | S | I | S |
| diethyl-ether | I | I | I |
| dioxane | S | Sh | S |
| chloroform | S | S | S |
| dichloromethane | S | S | S |
| chlorobenzene | S | Sh | S |
| ethyl acetate | Sh | I | S |
| acetone | I | I | I |
| 2-butanone | Sh | I | S |
| methanol | I | S | I |
| 95% ethanol | I | S | I |
| iso-butanol | I | S | I |
| 1-octanol | Sh | Sh | Sh |
| dimethyl-formamide | S | Sh | S |

* S = soluble; Sh = soluble near the b.p.; I = insoluble
** 50 mg of polymer were treated with 2 ml. of solvent. The poly-amido-amine was in a crystalline form.
*** Literature data for all the solvents listed but 1-octanol.

The same results were obtained with all the other polymers prepared according to this example, by utilizing all the other previously listed monomers (bis-acrylamides and amines), both from the standpoint of the physical properties and from the standpoint of the workability and anti-thrombogenicity presented by the articles obtained.

EXAMPLE 2

(A) By following exactly the procedures disclosed in the first part of Example 1, a poly-amide-amine having substantially the same structure as that of Example 1, except that it had end groups of the secondary amine type

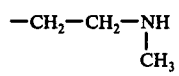

and not vinyl end groups, was prepared from 19.4238 grams of 1,4-bis-acrylyl-piperazine and 51.28 milliliters of a 2-molar aqueous solution of N,N'-dimethylethylendiamine. The molar ratio ($\mu$) between the two reagents was 0.975; however, dissimilarly from the case illustrated in Example 1, there was an excess amount of amine with respect to bis-acrylamide. The resulting poly-amide-amine still had $\overline{X}_n$ equal to about 79, but, as already mentioned, secondary amine end groups. By using the same procedures, poly-amide-amines having amine end groups and number average polymerization degrees ranging between 10 and 300 were prepared starting from the compounds already shown in Example 1, taking care of varying the excess amount of amine as a function of the desired average polymerization degree.

(B) To a solution of 17.51 grams of 2,4-toluendiisocyanate in 40 milliliters of anhydrous cyclohexanone, there were added dropwise under stirring 10.61 grams of anhydrous diethylenglycol and 5 grams of the polyamide-amine having $\overline{X}_n$ equal to about 79 and amine end groups described in the preceding paragraph, which were dissolved in 40 milliliters of anhydrous dimethylsulfoxide. Upon completion of the addition, the reaction mixture was heated to 115° C and kept at this temperature for 2.5 hours with an oil bath.

After this period of time, the reaction mixture was poured in about 2 liters of ether; the precipitate was washed with ether, then suspended in distilled water and washed several times by decantation with water, filetered and dried at 50° C and 0.1 mm Hg.

There were thus obtained 25 grams of a block copolymer, in the molecular structure of which there were present poly-amide-amine blocks having the above indicated structure and polyurethane blocks having the structure

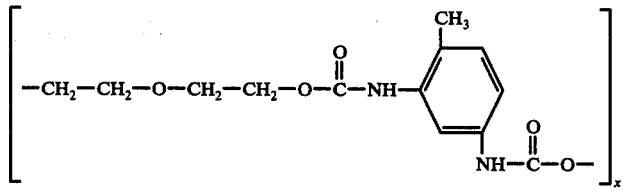

The elementary analysis of the copolymer showed the presence of 15% by weight of polyamidoamine blocks. By following exactly the same procedures, and utilizing the remaining poyamide-amines prepared as shown in Example 1-A, a whole series of polymers having amine end groups were prepared. The polymers thus obtained have physical properties different from those of the polyamide-amine and substantially corresponding to those of the polyurethanes.

Some test pieces which were prepared by extrusion from the foregoing polymers and implanted in the inferior vena cava of test animals, turned out to be permanently anti-thrombogenic.

EXAMPLE 3

1.4-Bis acryloyl piperazine (19.424; 0.1 moles) was treated with 49.00 ml of a 2-molar aqueous solution of methylamine, titrated against standard acid. The molar ratio between the amine and the bis-acrylamide was 0.98.

After stirring until a homogenous solution was obtained, the reaction mixture was left at room temperature (18°-20° C) for 2 days under an inert gas athmosphere. The very viscous solution was then poured into 500 ml of acetone. A gummy precipitate was obtained. This was separated by decantation, washed twice with 250 ml of acetone, and then dried at room temperature and 0.1 mm Hg. The poly-amido-amine so obtained had an intrinsic viscosity of 0.37 dl/g, measured in chloroform at 30° C. To a solution obtained by warming 10 g of the above poly-amido-amine in 90 ml of pure dimethyl formamide, 140 g of carefully purified styrene and 1.4 g azodiisobutironitrile were added. After purging with nitrogen, the mixture was left at 60° C under an inert gas athmosphere for 2 days, the product was then isolated by treating the reaction mixture with an excess of ether. The copolymer was then washed by trituration under ether, and it was extracted with water at room temperature for 2 hours. No water-soluble basic products were present in the aqueous phase (the free polyamidoamine is, in fact, very soluble in water). After drying under vacuum, the copolymer was then dissolved in chloroform and reprecipitated with an excess of an aliphatic hydrocarbon (pentane, hexane or heptane), and dried. The yield was about 105 g. The nitrogen content of the product was 1.68%. This indicates a poly-amido-amine content of about 9% by weight.

EXAMPLE 4

(a) A mixture of low-density polyethylene (20 g) and anhydrous benzene (250 ml) was refluxed until a clear solution was obtained. Sulfuril chloride ($SO_2Cl_2$) (8 ml) and azodiisobutyronitrile (1.2 g) were added, and the reaction mixture was then refluxed for further 4 hours. The total volume was then reduced to about 150 ml by partly distilling the solvent, and the mixture was poured into an excess of dry ether. The precipitated product was filtered and dried under vacuum to give 20.5 g of chlorosulfonated polyethylene, containing about 1% S and 4% Cl, as determined by elemental analysis. Different degrees of substitution could be achieved by using different quantities of sulfuril chloride and azodiisobutyronitrile. Other radical initiators, such as organic peroxides, could be used in place of the latter. U.V. irradiation was effective as well.

(b) N,N'-bisacryloylpiperazine (9.518 g, 0.049 moles) was dissolved in 25 ml of aqueous 2-molar solution of N,N'-dimethylethylenediamine. The mixture was left at room temperature, with occasional stirring, for two days, then it was poured into 200 ml of acetone. The precipitated product was separated by decantation and washed with 2 100-ml fresh portions of acetone. Finally, it was allowed to stand under acetone for several hours. Crystallization occurred, the gummy product turning into a white powder. This was collected by filtration and dried under high vacuum. A 95% yield of poly-amido-amine having $\overline{Mn} \simeq 15000$, and prevailingly end-capped with secondary amino groups, was obtained. By using a different molar ratio between N,N'-bisacryloylpipe razine and N,N'-dimethylethylenediamine, but always keeping an excess of the latter, poly-amido-amines similarly endcapped, but with different molecular weights, were obtained.

(c) Chlorosulfonated polystyrene (14 g), prepared as described under (a), was dissolved in dry, alcohol-free chlorofom (240 ml). A solution of secondary-amino end-capped polyamidoamine prepared as described under (b) (1.9 g) in dry, alchol-free chloroform (20 ml) was added, and the reaction mixture was stirred at 60° for 3 hours. The product was then isolated by pouring the reaction mixture into an excess of methanol containing a small amount of a base, filtering, and drying under vacuum. About 15 g of a graf copolymer, containing polyethylene and poly-amido amine blocks, was obtained. The poly-amido-amine content was about 12% by weight, as determined by elemental analysis of nitrogen. This copolymer was soluble in chlorofom, but insoluble in water, alcohols, and aliphatic hydrocarbons. Strong films could be obtained either by melt-pressing of the dry copolymer, or by slowly evaporating 5–30% chlorofom solutions on a suitable support.

By melt extrusion, or by casting from chloroform solutions, small tubes were obtained having the following dimensions: length, 25 mm; internal diameter, 8 mm; external diameter 1.2 mm. These were heparinized, and then implauted into the inferior vena cava of dogs, as described in example 2 The animals were sacrificed after 2–4 weeks. In no instances thrombous formation was found to occurr within the tubes.

EXAMPLE 5

By using chlorosulfonated polyethylenes having different degrees of substitution, and different amounts of poly-amidoamine in the last step, but otherwise following the previously described pattern, products containing from 3 to 35% by weight of poly-amido-amine blocks were obtained. Similarly products in which the $\overline{M}n$ of the poly-amido-amine blocks ranged between 3000 and 30000 were obtained by using in the last step a poly-amido-amine of corresponding $\overline{M}n$.

The same reaction pattern was followed in order to prepare copolymers containing, besides polyethylene blocks, blocks of anyone of the poly-amido-amines described in the previous examples.

It is apparent that, since the physical properties of the noval block copolymers substantially correspond to those of the polymers forming the blocks of conventional polymers, these latter should be selected in a suitable way depending on the physical characteristics of stiffness or flexibility, hardness or malleability which are necessary in view of the specific prosthesis or artificial organ to be produced.

What is claimed is:

1. Macromolecular materials suitable for forming antithrombogenic artificial organs characterized in that they are block polymers comprising polyamidic-aminic blocks and blocks from conventional polyaddition or polycondensation polymers.

2. Macromolecular materials according to claim 1, wherein the polyamidic-aminic blocks have the structure

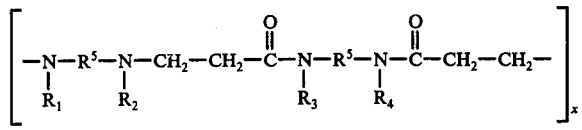

wherein $R_1$ and $R_2$ are alkyl or hydroxy-alkyl radicals with 1–6 carbon atoms, $R_3$ and $R_4$ are alkyl radicals with 1–6 carbon atoms, $R_5$ is an alkenyl radical with 1–12 carbon atoms, or together with $R_1$, $R_2$ and $R_3$, $R_4$ respectively and the nitrogen atoms to which it is linked, it forms an unsubstituted or substituted piperazine ring.

3. Macromolecular materials according to claim 1, wherein the polyamidic-aminic blocks have the structure

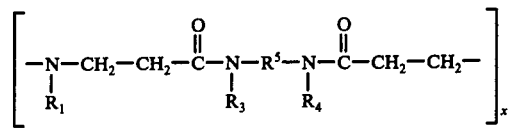

wherein $R_1$, $R_3$ and $R_4$ are alkyl radicals with 1–6 carbon atoms, $R_5$ is an alkenyl radical with 1–12 carbon atoms, or together with $R_3$, $R_4$ and the nitrogen atoms to which it is linked, it forms an unsubstituted or substituted piperazine ring.

4. Macromolecular materials according to claim 1, wherein the polyamidic-aminic blocks also comprise other monomers preferably selected from the group consisting of piperazine mono- and di-carboxylic acids, aliphatic amino-acids having 1–6 carbon atoms, allylamine and primary di-amines having from 2 to 12 carbon atoms.

5. Macromolecular materials according to claim 1, wherein the polyamidic-aminic blocks have end groups of the following kind

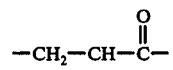

6. Macromolecular materials according to claim 1, wherein the polyamidic-aminic blocks have end group of the following kind

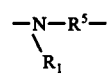

wherein $R_1$ and $R_5$ are as before defined.

7. Macromolecular materials according to claim 1, wherein the conventional polymer blocks are polyvinyl or polyvinylidene polyaddition polymers preferably selected from the group consisting of polystyrenes, polyacrylates, polymethacrylates, polyacrylamides, polyacrylonitrile and polyvinylacetate.

8. Macromolecular materials according to claim 1, wherein the conventional polymer blocks are polycondensation polymers preferably selected from the group consisting of polyamides, polyureas, polyurethanes and polyesters.

9. A process for preparing macromolecular materials suitable for forming antithrombogenic prostheses and artificial organs, which comprises:

(a) preparing a polyamidic-aminic prepolymer by polyaddition of amines having the formula

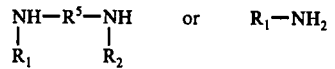

to bis-acrylamides having the formula

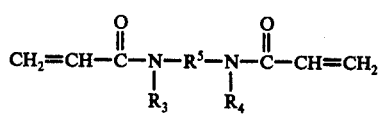

wherein $R_1$ and $R_2$ are alkyl or hydroxy-alkyl radicals with 1-6 carbon atoms, $R_3$ and $R_4$ are alkyl radicals with 1-6 carbon atoms, $R^5$ is an alkenyl radical with 1-12 carbon atoms, or together with $R_1$, $R_2$ and $R_3$, $R_4$ respectively, and the nitrogen atoms to which it is linked, it forms and unsubstituted or substituted piperazine ring;

(b) polymerizing a monomer or a mixture of monomers suitable to form thermoplastic polyaddition or polycondensation polymers in the presence of said polyamidic-aminic prepolymer.

10. A process according to claim 9, which comprises copolymerizing a polyamidic-aminic prepolymer having vinyl end groups with vinyl or vinylidene monomers.

11. A process according to claim 9, which comprises copolymerizing a polyamidic-aminic prepolymer having aminic end groups with a mixture of monomers suitable to form step polycondensation or polyaddition polymers.

12. A process according to claim 9, which comprises carrying out step (a) in water or an hydroxylated organic solvent, at temperatures of from 10° to 50° C, the reaction time varying from a few hours to some days.

13. A process according to claim 9, which comprises carrying out step (b) under polymerization conditions peculiar to the polymerization of monomers or mixtures of monomers suitable to form polyaddition or polycondensation thermoplastic polymers.

14. An antithrombogenic article useful in the biomedical field consisting of block macromolecular materials comprising polyamidic-aminic blocks and blocks of conventional poliaddition or polycondensation polymers, the surface of said materials being heparinized.

15. A process for manufacturing antithrombogenic articles according to claim 14, which comprises thermoforming said block macromolecular material comprising poliamidicaminic blocks and blocks of conventional polyaddition or polycondensation polymers by extrusion, molding and the like and heparinizing the surfaces thereof by immersing the articles in an aqueous, alcoholic or hydroalcoholic solution of heparin.

16. A process according to claim 15, wherein the heparin solution has concentration of from 0.1 and 20% and pH value of from 0 to 9.

* * * * *